United States Patent [19]

Bull et al.

[11] 3,989,599

[45] Nov. 2, 1976

[54] PROCESS AND APPARATUS FOR LIQUID AND GAS SEPARATION

[75] Inventors: Duncan C. Bull; Gerald L. Solomons, both of High Wycombe, England

[73] Assignee: Ranks Hovis McDougall Limited, London, England

[22] Filed: Aug. 16, 1974

[21] Appl. No.: 497,941

[30] Foreign Application Priority Data

Aug. 22, 1973 United Kingdom............... 39765/73

[52] U.S. Cl.............................. 195/105; 195/107; 195/127; 195/144
[51] Int. Cl.² ......................................... C12B 1/00
[58] Field of Search ........... 195/105, 107, 115, 136, 195/144, 127

[56] References Cited
UNITED STATES PATENTS

| | | | |
|---|---|---|---|
| 1,936,983 | 11/1933 | Lilly | 195/109 |
| 3,249,515 | 5/1966 | Rungaldier et al. | 195/107 |
| 3,586,605 | 6/1971 | Hosler | 195/115 |

FOREIGN PATENTS OR APPLICATIONS

| | | | |
|---|---|---|---|
| 7,011,552 | 4/1970 | Japan | 195/105 |
| 268,883 | 8/1970 | U.S.S.R. | 195/105 |

Primary Examiner—A. Louis Monacell
Assistant Examiner—C. A. Fan
Attorney, Agent, or Firm—Stevens, Davis, Miller & Mosher

[57] ABSTRACT

An apparatus and process for separating liquid and gas from a fermenter without allowing infecting organisms to penetrate back into the fermenter. A cyclone separator has a liquid outlet in its lower portion with an aseptic steam lock means which maintains liquid above minimum level to prevent passage of separated gas. Steam is fed through the outlet to sterilize it after opening. The gas is discharged through an outlet in the upper portion of the separator, the gas outlet also having aseptic lock means, preferably in the form of a steam jacket and valve on the gas outlet pipe.

9 Claims, 1 Drawing Figure

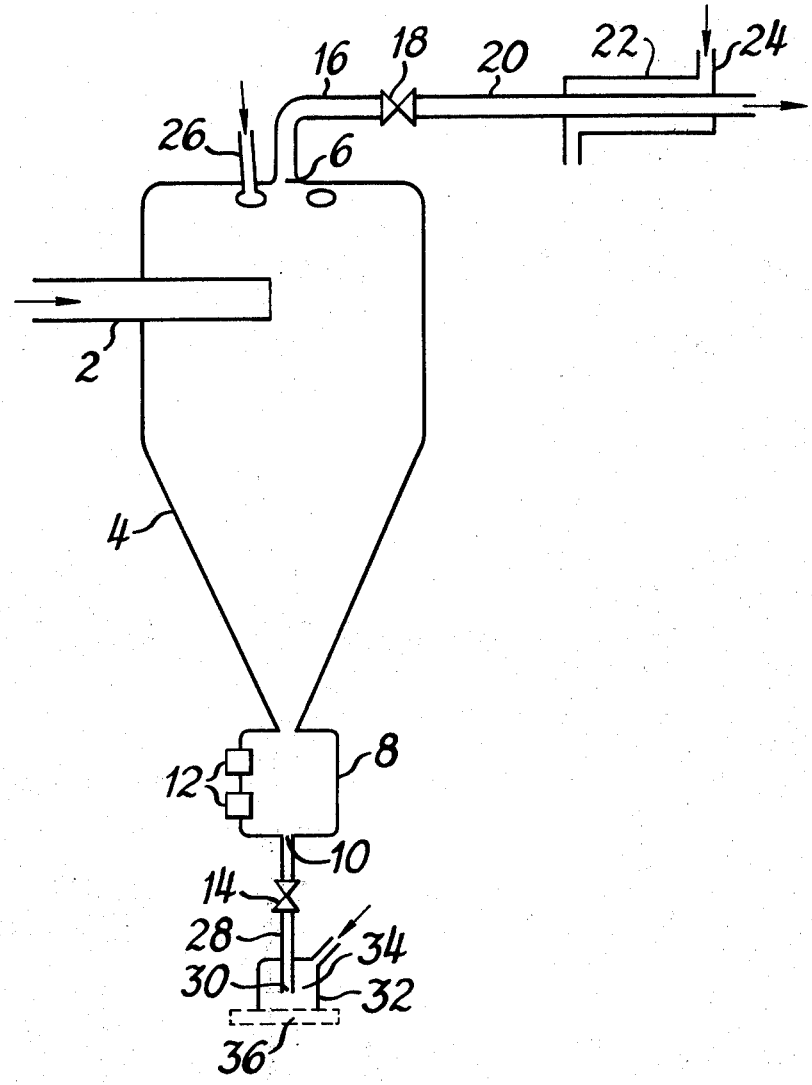

PROCESS AND APPARATUS FOR LIQUID AND GAS SEPARATION

The present invention relates to separation.

One of the major problems to be solved in operating an aseptic aerobic continuous fermentation is the removal of the product stream from the fermenter, without allowing infecting organisms to penetrate back into the fermenter.

This may be achieved by utilizing one aspect of the invention which consists in a separation process in which the liquid and gas in the output of a continuous aseptic aerobic fermenting process are separated from each other under aseptic conditions, and the separated gas and liquid are passed through aseptic lock means to non-aseptic conditions.

Another aspect of the invention consists in an arrangement for separating the liquid and gas in the output of a continuous aseptic aerobic fermenter from each other under aseptic conditions and aseptic lock means for passing the separated liquid and gas to non-aseptic conditions.

An advantage of the above is that the separator can be remote from the production vessels, but still allow aseptic separation to be obtained.

In experimenting with known separators, it was found that whatever aseptic lock means were tried it was impossible to make them efficient. This difficulty was solved according to another aspect of the invention by using a separation process in which the separated gas is prevented from being passed by an outlet for the separated liquid.

Another aspect of the invention consists in a continuous liquid/gas separator having a gas outlet and a liquid outlet and arranged to prevent the latter from passing the separated gas.

The term "liquid" as used herein includes a liquid slurry such as a culture broth.

In an embodiment of the invention, the separator can have any one or more of the following features, i.e. the separator is arranged to maintain a predetermined minimum level of the separated liquid above the aforementioned liquid outlet; includes level sensing means that operate a liquid outlet valve to maintain said level; is a cyclone separator; has a separating chamber provided with the aforementioned gas outlet and a settling chamber into which the separated liquid drains from the separating chamber before passing through the liquid outlet; includes a heating device for the gas outlet to prevent growback of micro-organisms, the heating device preferably being a steam jacket or direct steam injection; includes a heating device for the liquid outlet to prevent growback of micro-organisms, which heating device is or includes a steam seal and is or includes a bell-housing, which has a releasable closure enabling steam to be fed in through the liquid outlet for sterilizing the separator and after release of the closure to be used for the steam-seal, which closure may be a quick release cover.

The invention extends to apparatus including the aforesaid fermenter and a process being, or including the step of, continuous separation using any such separator, e.g. applied to the product of an aerobic fermentation, and the product of said arrangement, apparatus or process. An additional advantage of this separator is that it can be remote from production vessels but still allow aseptic separation to be obtained.

Reference will now be made by way of example to the accompanying drawing, the sole figure of which is a schematic view of a continuous liquid/gas cyclone separator embodying the invention and having the features described above.

Referring to the drawing, the separator has a tangential inlet 2 from the aseptic fermenter to a separating chamber 4 provided with a gas outlet 6 and draining into a lower settling chamber 8 having a liquid outlet 10 and level sensing probes 12 and an outlet valve 14 operated by the probes 12 to prevent the outlet 10 from passing gas by maintaining a predetermined minimum level of the separated liquid above the outlet 10.

After the air/culture broth enters the system through inlet 2, centrifugal force caused by the tangential entry causes the liquid to separate around the walls of the cyclone chamber 4, while the air goes to the middle and leaves through outlet 6 by an exit pipe 16 in the head of the cyclone after which it passes through a pressure reduction valve 18, since the system is at the pressure of the fermenter, usually around 15 p.s.i.g. The air then passes down a pipe 20 which is provided with a heater in the form of a steam jacket 22 with a steam line 24 at 20–100 p.s.i.g. steam so that no organisms can grow back up the pipe 20 and so infect the system. Also in the head of the cyclone is a water sparger 26, so that sterile water can be used to wash down the walls of the cyclone, to prevent any build-up of solids.

The liquid settles in the secondary chamber 8 and the height of the liquid in this chamber is controlled so that the chamber is never totally empty of liquid. This is necessary so that air never leaves the cyclone from the bottom valve 14, only through its own valve 18 as described above. The reason for this is that air/liquid mixture leaving a pressure vessel always causes severe splashing and this must be avoided to prevent contamination. Level probes 12 in the chamber 8 control the opening valve 14 which is placed in the exit pipe 28 in such a manner as to ensure the minimum of turbulation in the pipe at the exit point 30. The liquid can leave the system in an on/off manner or as a continuous modulated stream, depending on the configuration of the level sensing probes in chamber 8, and provided the flow rate causes the minimum of turbulence. Various other types of level control can be used, the most important point being that they can operate aseptically and they do not allow solids build-up. Probes 12 are preferably such that they do not actually enter the chamber, but work through the walls, e.g. gamma radiation probes. A simple reliable system can operate using one probe only, but the preferred system uses two.

After passing through the exit valve 14, the liquid leaves the system through a heating device in the form of a steam seal such as a bell-housing, the outer chamber 34 of which is under a flow of steam which also serves to wash down the walls of the housing. Since the liquid leaves the exit point 30 and passes through the steam in chamber 34 quickly, any temperature rise is negligible, i.e. not detrimental.

In operation, a releasable closure in the form of a quick release cover 36, shown in chain lines, is placed over the exit of bell housing 32 and valve 14 opened in order to allow the whole system to be sterilized at 15 p.s.i.g. of steam pressure. After the sterilization process, the direct exit valve 14 is closed and the cover removed so that on stream operation can begin.

It will be seen that inlet 2 can be connected to a continuous aerobic aseptic fermenter (not shown) for the liquid and gas in the output thereof to be separated from each other in the separator under aseptic conditions and passed through aseptic lock means, heaters 22 and 32, to non-aseptic conditions without allowing growback into either outlet and, in the case of heater 22, in such a manner as to prevent labile material from becoming denatured.

The fermentation may be applied to micro-fungal organisms, e.g. as disclosed in our co-pending U.S. Pat. application No. 459,021 filed Apr. 8, 1974.

What we claim is:

1. A continuous separator for liquid and gas for obtaining a fermentation product from a continuous fermenter by way of the separator, comprising:
    a cyclone separator chamber having an inlet from the fermenter in the upper portion of the chamber;
    a liquid outlet in the lower portion of the chamber, the outlet having aseptic lock means comprising a liquid outlet valve and control means responsive to a liquid parameter for maintaining the separated liquid above a minimum level above the valve to prevent passage of separated gas and a heating device having a releasable closure and means to feed steam in through the liquid outlet for sterilizing the separator and after release of the closure to be used as an aseptic lock means;
    a gas outlet in the upper portion of the chamber having aseptic lock means.

2. A separator as claimed in claim 1, in which said control means comprise means for providing an intermittent output of liquid from said liquid outlet.

3. A separator as claimed in claim 1, in which the liquid outlet aseptic lock means comprise means for providing a fluid seal.

4. A separator as claimed in claim 3, in which the liquid outlet aseptic lock means comprise means for providing the fluid seal in the form of a steam seal.

5. A separator as claimed in claim 4, in which the liquid outlet aseptic lock means is positioned so that the effluent liquid falls through the steam seal under gravity.

6. A separator as claimed in claim 1, in combination with a continuous aseptic aerobic fermenter, for separating the liquid and gas in the output of the fermenter.

7. A separator as claimed in claim 5, in combination with a continuous aseptic aerobic fermenter, for separating the liquid and gas in the output of the fermenter.

8. A separation process in which the liquid and gas in the output of a continuous aseptic aerobic fermentation process are separated from each other under aseptic conditions said process comprising passing the liquid and gas into a tangential inlet in the upper portion of a cyclone separator chamber having a gas outlet and a liquid outlet, separating the gas and liquid by centrifugal force, maintaining the separated liquid above a minimum level above an outlet valve in the lower portion of the chamber, preventing the gas from being passed out with the separated liquid by maintaining said liquid level, releasing a portion of said liquid through said valve to an aseptic steam lock means, sterilizing the separator by passing steam through said aseptic steam lock means, passing said gas from said chamber through said gas outlet while maintain an aseptic gas lock on gas outlet by heating it so that no organisms can grow back up the gas outlet.

9. A process as claimed in claim 8, in which the liquid effluent falls through the aseptic steam lock means under gravity.

* * * * *